United States Patent [19]

Motoyama et al.

[11] Patent Number: 4,751,241

[45] Date of Patent: Jun. 14, 1988

[54] PHARMACEUTICAL COMPOSITION OF CYCLANDELATE HAVING A HIGH DEGREE OF BIOAVAILABILITY

[75] Inventors: Shimesu Motoyama; Satoshi Sato; Seiichi Umeda; Hirotsune Yasumi; Emiko Sudo; Takuichi Tsujino, all of Tokyo; Akira Akazawa, Tokushima, all of Japan

[73] Assignee: Freund Industrial Company, Ltd., Tokyo, Japan

[21] Appl. No.: 724,502

[22] Filed: Apr. 19, 1985

Related U.S. Application Data

[63] Continuation of Ser. No. 394,180, Jul. 1, 1982, abandoned.

[30] Foreign Application Priority Data

Jul. 14, 1981 [JP] Japan .................. 56-109777
Nov. 11, 1981 [JP] Japan .................. 56-175168

[51] Int. Cl.$^4$ .................................. A61K 31/235
[52] U.S. Cl. ........................ 514/532; 514/937
[58] Field of Search ........................ 514/532

[56] References Cited

U.S. PATENT DOCUMENTS

| 3,932,634 | 4/1976 | Kardys | 514/168 |
| 3,966,632 | 6/1976 | Colliopoulos et al. | 424/365 |
| 4,073,943 | 2/1978 | Wretlind et al. | 514/938 |
| 4,327,076 | 4/1982 | Puglia et al. | 424/38 |
| 4,327,077 | 4/1982 | Puglia et al. | 424/38 |

FOREIGN PATENT DOCUMENTS 57-004916 1/1982 Japan .

Primary Examiner—Albert T. Meyers
Assistant Examiner—F. Krosnick
Attorney, Agent, or Firm—Oblon, Fisher, Spivak, McClelland & Maier

[57] ABSTRACT

An oral pharmaceutical composition which comprises a polyglycerol ester of an unsaturated fatty acid and a drug which is very slightly soluble in water.

6 Claims, 5 Drawing Sheets

PHARMACEUTICAL COMPOSITION OF CYCLANDELATE HAVING A HIGH DEGREE OF BIOAVAILABILITY

This application is a continuation of application Ser. No. 394.180, filed July 1, 1982, now abandoned.

BACKGROUND OF THE INVENTION

Field of the Invention

The present invention relates to oral pharmaceutical compositions which have a high degree of bioavailability because of their good absorptivity in the digestive tract.

SUMMARY OF THE INVENTION

One object of the present invention is to provide a novel pharmaceutical composition which possesses a high degree of bioavailability.

Another object of the present invention is to facilitate the absorptivity of a drug which is only very slightly soluble in water by a polyglycerol ester of an unsaturated fatty acid.

These objects and other objects of the present invention as hereinafter will become more readily apparent can be attained by an oral pharmaceutical composition which comprises a polyglycerol ester of an unsaturated fatty acid and a drug which is very slightly soluble in water.

In a specific embodiment of the invention the oral pharmaceutical composition comprises a drug which is very slightly soluble in water dispersed in a polyglycerol ester of an unsaturated fatty acid.

In another specific embodiment of the invention the oral pharmaceutical composition comprises a polyglycerol ester of an unsaturated fatty acid and a drug which is very slightly soluble in water dispersed in an oily substance.

In still another embodiment of the invention the oral pharmaceutical composition comprises a polyglycerol ester of an unsaturated fatty acid and a drug encapsulated in microcapsules each having a diameter less than three millimeters.

In yet another embodiment of the invention the oral pharmaceutical composition comprises a polyglycerol ester of an unsaturated fatty acid and a drug, wherein the drug which is dispersed in the polyglycerol ester of an unsaturated fatty acid is adsorbed on a powder.

The high degree of bioavailability of the composition of the present invention is attributable to the surface action properties of the polyglycerol ester of an unsaturated fatty acid component of the composition.

BRIEF DESCRIPTION OF THE DRAWINGS

A more complete appreciation of the invention and many of the attendant advantages thereof will be readily obtained as the same becomes better understood by reference to the following detailed description when considered in connection with the accompanying drawings, wherein.

DETAILED DESCRIPTION OF THE PREFERRED EMBODIMENTS

The central feature of the present invention is a pharmaceutical composition which contains a drug which is only very slightly soluble in water. Yet the present pharmaceutical composition is characterized by a high degree of bioavailability.

The polyglycerol ester of an unsaturated fatty acid component of the present composition is hereinafter referred to as PGUFA ester or simply as PGUFAE. Suitable examples of PGUFAE include diglycerol monooleate, diglycerol monolinolenate, triglycerol monooleate, octaglycerol dioleate, decaglycerol decaoleate, pentaglycerol monolinoleate and the like. Suitable examples of the unsaturated fatty acid component of the ester include oleic acid, linoleic acid, linolenic acid and other unsaturated fatty acids having eight to twenty-two carbon atoms. The polyglycerol ester of ricinoleic acid is a substitute for the polyglycerol ester of oleic acid, linoleic acid, linolenic acid or other unsaturated fatty acid.

Suitable examples of drugs which are very slightly soluble in water include ajmaline, ibuprofen, erythromycin, erythromycin stearate, erythromycin ethyl succinate, kitasamycin, chloramphenicol palmitate, ergocalciferol ($V.D_2$), cholecalciferol ($V.D_3$), progesterone, testosterone enanthate, testosterone propionate, methyltestosterone, ethinylestradiol, d-camphor, tocopherol, halothane, phytomenadione ($V.K_1$), rivoflavinterabutyrate, tocopherol acetate, medroxyprogesterone acetate, 1-isopropyl-7-methyl-4phenyl-2 (1H)-quinazolinone (1MPQ), nifedipine, indomethacin, dipyridamole, d-limonene (Liq.), tricaprylin (Liq.), tocopherol nicotinate, oxyphenbutazone, fluphenazine enantate, ethyl aminobenzoate, lidocaine, niceritrol, nitroglycerin, clofibrate (Liq.), phenylpropanol, linoleic acid (V.F), benzonatate, creosote (Liq.), guaiacol (Liq.), vitamin A, cychlocumarol, menatetrenone ($F.K_2$), cinnarizine, cyclandelate, $CoQ_4$, $CoQ_7$, $CoQ_9$ and $CoQ_{10}$ (ubidecarenone).

The drugs which can be used in the composition of the present invention are not limited to the drugs mentioned above. Besides drugs, the present composition can also be based upon the combination of natural nutrients which are only very slightly soluble in water with the polyglycerol ester of an unsaturated fatty acid. Suitable examples of natural nutrients include vitamin A, vitamin D or vitamin E rich natural oil, shark liver oil (squalene rich oil), and the like. The polyglycerol radical of the polyglycerol ester of an unsaturated fatty acid component of the present composition has at least one hydroxy radical.

The term "a lymphatic-absorbable, oil-soluble drug" in this specification means a drug which is easily absorbable in the lymphatic system and in the intestinal canal and which is soluble in oil and fat. Suitable examples of lymphatic absorbable, oil-soluble drugs include vitamin A, vitamin D, vitamin E, vitamin K, $CoQ_4$, ubiquinone-7, ubiquinone-9, ubidecarenone and the like.

The term "an oily substance" in this specification means a substance which is an oil or fat or analogue thereof. Suitable examples of oily substances include sesame oil, rape oil, soybean oil, essential oil, lard, tallow, squalene, squalane, caraway oil, cinnamon oil, spearmint oil, 1-carvone, phospholipid, glycolipid and mixtures thereof. The substance "1-carvone" is the main component oil of spearmint oil and is colorless or a light yellow colored oil, having a boiling point of 230° C.

The term "powder" in this specification includes only those powdered materials which are nontoxic such as, for example, lactose powder, $\beta$-cyclodextrin, microcrystalline-cellulose, starch, wheat flour, dextrin, cellulose-powder, powdered silicon dioxide and mixtures thereof.

The term "water-soluble high molecular weight substance" in this specification includes such substances as: $\alpha$-starch, carboxymethyl starch, pullulan, gelatin, gum arabic, carboxymethyl cellulose, hydroxypropyl cellulose, polyvinyl alcohol, polyvinyl pyrrolidone, and the like.

The term "very slightly water soluble drug" includes only those drugs which are very limitedly soluble in water.

The present invention is the latest in a series of inventions which have resulted from an ongoing study of how to facilitate the absorption of a drug which is only very slightly soluble in water in the body. Earlier inventions directed to related compositions and processes include: U.S. patent application Ser. No. 139,750 filed 1980, Japanese patent application No. (hereinafter abbreviated as J. Pat. Appl. No.) 70104/80, filed May 28, 1980; J. Pat. Appl. No. 118135/80, filed Aug. 27, 1980; J. Pat. Appl. No. 146362/80, filed Oct. 21, 1980; J. Pat. Appl. No. 27663/81, filed Feb. 28, 1981 and J. Pat. Appl. No. 109,777/81, filed July 14, 1981.

The present invention is the result of a study on how to facilitate the absorption of a drug which is very slightly soluble in water with a surface active agent. Surface active agents which have been studied include anionic surface active agents such as the alkaline salts of higher fatty acid esters (soap) and the salts of alkyl sulfonic acids; and cationic surface active agents, such as invert soap, salts of higher amine halogeno-acids and salts of quaternary ammonium bases; and nonionic active agents such as polyethylene glycol alkyl ether, polyethylene glycol fatty acid ester and sorbitan fatty acid ester and the like. However, the anionic surface active agents and the cationic surface active agents cannot be used as a surface active agent in combination with nutrients or for drugs because of their toxicity or because of other reasons. Consequently, surface active agents which belong to the polyoxyethylene group are prohibited for use in foods. However, for pharmaceutical use, polyoxyethylene hydrogenated castor oil and polyoxyethylene sorbitan monooleate are free of restrictions. Nevertheless, recently it has been reported that in some cases nonionic surface active agents, which are used in pharmaceutical applications, have many drawbacks such as exhibiting hemolytic properties, mucosa-irritativeness and so on. Because of these problems, one hesitates to use these surface active agents as polyoxyethylene hydrogenated castor oil and polyoxyethylene sorbitan monooleate in drug preparations. Currently, there is a strong demand for the development of harmless surface active agents which can be readily used in pharmaceutical compositions.

The inventors of the present application searched several hundreds of surface active agents and found that polyglycerol esters of fatty acids which have only recently been authorized for use in foods by the FDA of the United States of America are very effective surface active agents. The properties of these esters have been evaluated.

Polyglycerol esters of fatty acids (hereinafter abbreviated as PGFA esters or PGFAE) can exhibit a variety of HLB values depending on the degree of polymerization of glycerin and the degree of esterification of polyglycerin and also by the properties of the fatty acid component. It has now been discovered that PGFA esters very readily emulsify or solubilize drugs which are only very slightly soluble in water. Furthermore PGFA esters are nontoxic and harmless to the human body. These discoveries are disclosed in J. Pat. Appl. No. 109777/81, filed July 14, 1981 which application has already been referred to in this specification.

The benign characteristics of PGFAE are consistent with the fact that its monomeric progenor, glycerin, is a natural substance quite unlike polyoxyethylene and derivatives thereof such as polyoxysorbitan monooleate which have been used in the past as surface active agents in pharmaceutical compositions.

In a more specific aspect of the invention as described in J. Pat. Appl. No. 109777/81, the surface active agent is directed to those compounds which are based upon oleic acid, linoleic acid, ricinoleic acid or linolenic acid as unsaturated fatty acids especially when the bioavailability of the compositions is considered.

The compositions of the present invention are effective in improving the bioavailability of the drug which is present in the same as a result of the surface active properties of the polyglycerol ester of an unsaturated fatty acid ester component of the composition.

The present composition is even more effective when a drug, which is very slightly soluble in water, is dispersed in PGUFAE because in that case the drug is readily emulsified in the digestive organs. The degree of dispersion of a drug in PGUFAE depends on the mutual affinity of both components and on the degree of agitation when dispersed. The higher the degree of dispersion, the more favorable the composition. Consequently, a solution which is a molecular dispersion, is the most favorable dispersion.

The ratio of drug to PGUFAE in the composition is a function of the dispersibility of the drug. Usually, 0.05~30 parts by weight of the PGUFAE are combined per one part by weight of the drug.

The examples of the present application actually describe compositions in which the drug and the PGUFAE are dispersed in a liquid oily substance. Compositions such as these examples are even more effective for increasing the bioavailability of the drug. These compositions can be prepared by adding a drug which is very slightly soluble in water and a PGUFAE to an oily substance and agitating the resulting mixture. If the drug is solid, the drug should be preferably pulverized before it is added to the oily substance. The specific amount of drug combined with an oily substance is determined on a case by case basis, depending on the dispersibility of the drug in the oily substance. Generally, it is preferable to use 0.5~10 parts by weight of the oily substance per one part of the drug. Hundreds of experiments have indicated that the preferred ratio of a PGUFAE to a drug is within the range of 0.1~5 parts (wt) per one part (wt) of drug.

In these compositions in which the drug is dispersed in a liquid PGUFAE, or the drug and the PGUFAE are dispersed in an oily substance, it is possible to increase the bioavailability of the drug by encapsulating the composition in microcapsules having a diameter less than 3 millimeters. The effectiveness of these microcapsules is mentioned in J. Pat. Appl. No. 118135/80 filed Aug. 27, 1980 and in J. Pat. Appl. No. 146362/80 filed Oct. 21, 1980. The microencapsulated composition is more effective for increasing the bioavailability of the drug than when the drug is encapsulated in the more conventional larger sized capsules. The reason why the microencapsulated composition is more effective, is not obvious, but it may be for the following reasons. Generally, oily substances have a strong surface tension, and an important first step is the break up of the oil for the emulsification of the oil in the digestive organs. When an oily substance is orally administered, it is subjected to agitation by the actions of the stomach and intestines, which action facilitates the break up of the oil into smaller particles. However, the agitation by the internal organs is not as strong as that of external mechanical agitation of the oil. Consequently, when an edible oil is ingested by a subject, quite often nearly undigested oil is excreted by the person.

The oral administration of the oily composition in microcapsule form has the effect of breaking up the oily composition into small particles. Therefore, even a patient or an aged person who has a weak bile and lipase secretion power and whose agitative power of the digestive organs is weakened, can easily emulsify an oily substance if it is administered in the form of microcapsules. Consequently, it is believed that the drug is more smoothly absorbed into the blood and directly into the lymphatics of a patient or an aged person. This hypothesis is supported by the fact that when the particles are broken down into smaller fragments, the surface area of the particles greatly increases.

The limitation of less than 3 millimeters diameter for the microcapsules has the effect of increasing the absorption of the drug because the surface area of the oily composition is increased. Moreover, the microcapsule form of the drug provides for the convenient handling of the pharmaceutical composition. Actually, microcapsules having a 3 mm diameter can be adjusted with respect to dosage amounts of a drug for an adult or for a child as well as for patients who require lesser or greater amounts of drug depending upon the condition of the patient by simply varying the amount of microcapsules administered. Microcapsules having a diameter of 0.1~1 mm are available as granula. Moreover, microcapsules having a diameter under 1 mm can be encapsulated in capsulate operculatae (usual capsule) or can be used as granula subtilae or pulvere. It is difficult to form microcapsules having a diameter under 3 millimeters by the typical commercial procedures for producing capsules or soft capsules because the methods are uneconomical and because the balance of wall material to drug is difficult to control or maintain. Consequently, for the production of microcapsules it is appropriate to use the seamless microcapsule technique.

Figure 1:
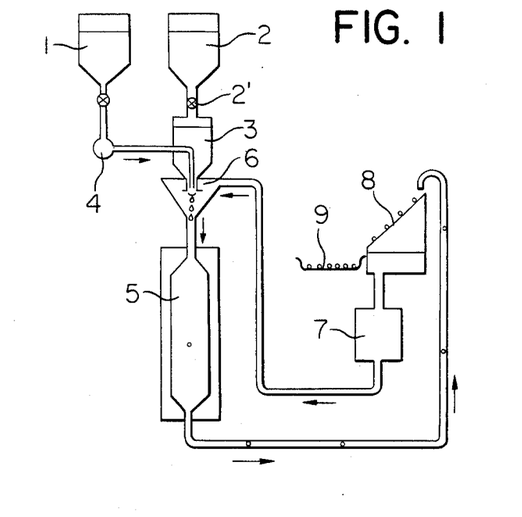
FIG. 1 is an illustration showing how to manufacture seamless microcapsules by the Globex Mark II capsule-making apparatus.

For the production of seamless microcapsules, it is convenient to use the Globex Mark II microcapsule apparatus, which is marketed by the Miniture Trading Co., Ltd. (Ienroku Hankyu Bldg., 1-10, 7-chome, Tenjinbashi, Oyodo-ku, Osaka, Japan). With this apparatus seamless microcapsules are produced, using a gelatin solution as the wall forming material. Referring to FIG. 1, the process of preparing the microcapsules is described as follows: (i) The apparatus is charged with a liquid system (1) of a very slightly soluble drug which is dispersed in an oily substance or in a liquid PGUFAE. (ii) The apparatus is charged with a heated aqueous gelatin solution (2). (iii) The action of the pulse pump (4) and the closing valve (6) are synchronized such that drops of globular gelatin capsules are formed one by one in the cooling oil (5). (iv) The resulting microcapsules are cooled to solidify the walls of the microcapsules. (v) The cooled capsules are carried by circulating oil onto the sieve (8) and the capsules are then gathered into receptacle (9), after removal of the residual oil.

An improved apparatus is disclosed in J. Pat. Publication No. 1067/78. A drug of the present invention is easily absorbed directly in the lymphatics after being emulsified in the small intestines by bile and pancreatic juice, if the drug is a lymphatics-absorbable, oil-soluble drug.

It is very advantageous if the drug is absorbed directly into the lymphatics without absorption into the bloodstream, because in that case the drug is not metabolized by the liver after being carried to the liver through the portal vein. Besides the absorption of the drug in the lymphatics, some part of the lymphatics-absorbable, oil-soluble drug is absorbed in the blood. This combination increases the bioavailability of the drug to the body.

As was previously mentioned, vitamin A, vitamin D, vitamin E, vitamin K, $CoQ_4$, $CoQ_7$, $CoQ_9$, $CoQ_{10}$ and the like are examples of lymphatics-absorbable, oil-soluble drugs.

A powder which has absorbed the system of a PGUFA ester in which a very slightly soluble drug is dispersed efficiently promotes emulsification of the system in the digestive organs, because the system is finely dispersed on the surface of the minute particles of the powder. Consequently, a composition of this sort is advantageous for increasing the bioavailability of the drug, because the absorption of the very slightly soluble drug from the powder is accelerated. If the very slightly soluble drug which is present in this composition is a lymphatics-absorbable, oil-soluble susbstance, the absorption of the drug by the lymphatics is increased.

To adsorb the PGUFA ester dispersion system on a powder, it is necessary that the system be liquid. No special methods are required to adsorb the system on a powder. However, a preferred procedure is to spray the liquid system of the PGUFAE on the powder.

It is desirable to prepare a powdered composition. Usually, a satisfactory powdered composition is obtained by using less than one weight part of the liquid system to one weight part of the powder.

A composition which is prepared by the steps of: (1) dispersing a very slightly soluble drug and PGUFA ester in an oil; and (2) adsorbing the resulting dispersion on a powder; is not claimed in the present specification. However, such a dispersion technique is effective for increasing the bioavailability of the very slightly soluble drug for nearly the same reason as the above-mentioned composition.

An embodiment of the composition of the present invention which is prepared by the steps of: (1) dispersing a very slightly soluble drug in a polyglycerol ester of an unsaturated fatty acid; (2) emulsifying the resulting dispersion in water; or (3) emulsifying the resulting dispersion in water in the presence of a water soluble high molecular weight substance, when it is necessary for emulsification; and (4) removing the water from the resulting emulsion is effective for increasing the bioavailability of the drug. In the fourth step (4) of the preparation of the composition, the composition is preferably sprayed in order to remove water from the emulsion.

Specifically, the composition can be prepared by the steps of:

(1) dispersing a vey slightly soluble drug in a polyglycerol ester of an unsaturated fatty acid ester;

(2) dissolving the resulting dispersion in a volatile organic solution of a water-soluble high molecular weight substance; and (3) removing the volatile organic solvent from the solution.

Alternatively, the composition can be prepared by the steps of:

(1) dissolving a drug which is very slightly soluble in water and a polyglycerol ester of an unsaturted fatty acid in a volatile hydrophobic organic solvent;

(2) emulsifying the resulting organic solvent soltution in water optionally in the presence of a water-soluble high molecular weight substance, when it is necessary for emulsification; and (3) removing the water and the volatile hydrophobic organic solvent from the emulsion.

It is necessary to decrease the size of the particles of the drug in any way practical to accelerate the absorption of a very slightly soluble drug. In the case of a lymphatics-absorbable, oilsoluble drug, it is known that the drug is absorbed in the lymphatic system after being emulsified and micellized in the small intestine by bile and lipase. The lymphatics absorption ratio of the drug in vivo is determined by measuring the lymph which collects through canula from lymphatics by the Bollman method. Instead of measuring the absorption in vivo, a preparatory measurement in vitro is useful, which depends on the measurements of the mycelle formation of the composition of the drug in a solution of bile acid salt by passing through minute pore filters. The bioavailability increasing power of a PGUFAE can be estimated by ascertaining the emulsifying power of the PGUFAE for a very slightly soluble drug by measuring the particle size of the emulsion using minipore filters.

Having now generally described this invention, a further understanding can be obtained by reference to certain specific examples which are provided herein for purposes of illustration only and are not intended to be limiting unless otherwise specified.

EXAMPLE 1

Figure 2:
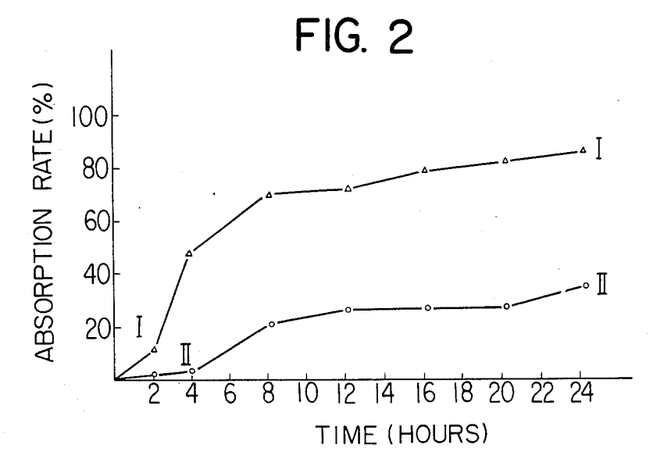
FIG. 2 is a diagram illustrating the results obtained from the test of Example 1.

Twenty grams of d,l- α-tocopherol acetate were dissolved in 80 g of decaglycerol decaoleate (Santone ® 10-10-0 Durkee Ind. Foods SCM Ltd.) with heat. The Globex Mark II capsule-making apparatus of FIG. 1 was charged with this solution. Then seamless microcapsules which have a diameter of about 1 mm were produced by the apparatus. The content of tocopherol in the capsules was 15 wt %. Santone is the product of Durkee Ind. Foods SCM Ltd. as is mentioned above. In subsequent portions of the specification only the tradename Santone is mentioned omitting the name of the company. Lymph absorbability of the composition of this example, when it was administered orally to rats, was measured by the Bollman method. A quantity of the composition which contained 5 mg of d,l- α-tocopherol acetate was administered orally to each of five rats (average weight was 300 g). After 24 hours of continuous collection of the lymph from each rat through a canula which was previously connected with each rat's lymphatic system, tocopherol in all lymph samples was measured. For a control sample an aqueous suspension of d,l- α-tocopherol acetate, which was prepared by forced agitation, was administered orally to rats. The results thus obtained are illustrated in FIG. 2 where the curves I—I and II—II represent the composition of Example 1 and the control suspension, respectively.

EXAMPLE 2

Eighty grams of erythromycin stearate were dissolved in 120 g of purified 1-carvone at ca. 50° C. A liquid composition was provided by adding to this solution 50 g of pentaglycerol monooleate (tradename SY-Glyster-MO-500, a product of Sakamoto Pharmaceutical Co., Japan). Separately, 45 parts of gelatin and five parts of glycerin were dissolved in 50 parts of purified water with heat (prescription 1). Further, eight parts of mefhyl acrylate, and methacrylic acid copolymer were dissolved in 92 parts of three wt % aqueous solution of sodium carbonate (prescription 2). A 0.6 mm thick gelatin sheet was produced by using a mixture of the above-mentioned prescription 1 and prescription 2 solutions by the "flat plate" process. The ratio of the two solutions was 95:5 by volume. Soft capsules were manufactured by the steps of (1) pouring into each dent of the gelatin sheet 250 mg of the above-described liquid composition of erythromycin, (2) covering another gelatin sheet, (3) setting a frame on the gelatin sheets, and (4) pressing on the sheets with a press. By this procedure capsules containing 80 mg of erythromycin stearate were prepared.

EXAMPLE 3

After the Globex Mark II capsule making apparatus was charged with the liquid composition of erythromycin stearate which is mentioned in Example 2, globular microcapsules having a 2.8 mm diameter were produced by the apparatus which is illustrated in FIG. 1. The content of erythromycin in the capsules was 25 wt %.

Figure 3:
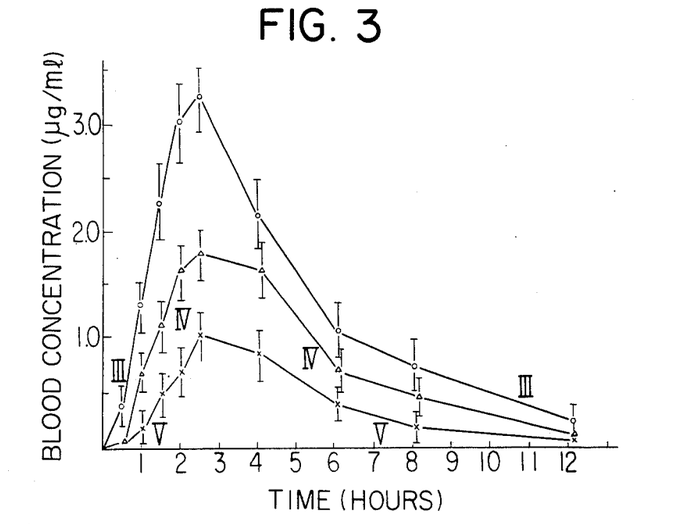
FIG. 3 is a diagram illustrating the results obtained from the tests of Examples 2 and 3.

To test the activation degree of the compositions of Example 2 and Example 3, these compositions and, as a control, commercial tablet preparations of erythromycin stearate were separately administered orally after four hours fasting to 5 adult male human subjects in a dose of 500 mg of erythromycin stearate. The erythromycin content in the blood of each subject was measured 12 hours after administration of the drug. The content of erythromycin stearate in a tablet of the commercial preparation which was used as the control was 250 mg. The results thus obtained are illustrated in FIG. 3 where the curves III—III, IV—IV and V—V represent the composition of Example 3, Example 2 and a commercial tablet, respectively.

EXAMPLE 4

A liquid composition was obtained by dissolving 50 g of phytonadione (V.K$_1$) in a liquid mixture of 50 g of octaglycerol monooleate (Santone ® 8-1-0) and 50 g of triglycerol trioleate (SY-Glyster-TO-310 manufactured by Sakamoto Pharamceutical Industrial Co., Japan). This liquid composition is available for soft capsule drugs and for liquid drugs.

EXAMPLE 5

A 15% phytonadione powdered drug was prepared by adsorbing 250 g of the liquid composition of Example 4 on 750 g of Adsorider-101 (manufactured by Freund Ind. Co., Ltd., Japan).

EXAMPLE 6

A liquid composition was obtained by dissolving 20 g of ubidecarenone powder in a mixture of 50 g of purified l-carvone and 20 g of decaglycerol decaoleate (Santone® 10-10-0) with heat.

EXAMPLE 7

The Globex Mark II capsule-making apparatus of FIG. 1 was charged with the liquid composition of Example 6 and an aqueous gelatin solution which was prepared by slowly mixing 100 g of gelatin and 35 g of gum arabic in purified water. Then, seamless microcapsules which have diameter of 1 mm were manufactured by the Globex Mark II apparatus.

EXAMPLE 8

A liquid composition was prepared by dissolving 10 g of powdered ubidecarenone in 40 g of triglycerol monooleate (SY-Prister-MO-500 manufactured by Sakamoto Pharmaceutical Ind. Co., Japan) with heat.

EXAMPLE 9

Fifty grams of the liquid composition of Example 8 were heated to 50° C. This composition was added into 150 g of minutely crystallized cellulose powder (Abicell manufactured by Asahi Kasei Co. Ltd., Japan) which was previously heated to 50° C. A 5% ubidecarenone powdered drug was obtained by stirring the resulting mixture and adsorbing the liquid composition of Example 8 on the crystallized cellulose powder.

The rate of dispersion in water and micelle formation ability in a mixed bile acid salts solution of the pharmaceutical compositions of Example 5, Example 8 and Example 9 were measured by the following technique. (The mixed bile acid salt solution, mentioned above, is a mixed solution of 15 millimole concentration of sodium salts of taurocolic acid and deoxytaurocolic acid, wherein the mole ratio of the two acid salts is 1:1.)

One gram of each composition of Examples 5, 8 and 9 was added to 30 ml water and to 30 ml of mixed bile acid salts solution separately. Each solution was agitated at 37° C. The resulting dispersions were successively filtered, at first through a 5 $\mu$ millipore filter, and next through a 0.45 $\mu$ millipore filter. The rate of dispersion and the micelle formation ability of each composition was determined by measuring the weight of drug which passed through the 0.45 $\mu$ millipore filter. As for controls, one gram samples of raw phytonadione and raw ubidecarenone were treated separately by the same process as described above. The results obtained are shown in Table 1.

TABLE 1

| Shaking Time | Rates of Dispersion and Micelle Formation Degree (Percent) | | | | | | | |
|---|---|---|---|---|---|---|---|---|
| | 5 minutes | | 10 minutes | | 30 minutes | | 60 minutes | |
| Group | A | B | A | B | A | B | A | B |
| Example 5 | 61.4 | 64.9 | 65.9 | 70.1 | 71.3 | 72.8 | 73.5 | 75.6 |
| Control | 4.1 | 4.7 | 4.1 | 4.7 | 4.2 | 4.7 | 4.1 | 4.7 |
| Example 8 | 56.6 | 58.9 | 69.3 | 71.4 | 78.4 | 79.3 | 81.7 | 85.8 |
| Control | 0.1 | 0.1 | 0.2 | 0.3 | 0.2 | 0.3 | 0.3 | 0.4 |
| Example 9 | 61.4 | 66.7 | 76.5 | 80.1 | 85.5 | 89.6 | 86.7 | 93.5 |
| Control | 0.1 | 0.1 | 0.2 | 0.3 | 0.2 | 0.3 | 0.3 | 0.4 |

The "A" groups of figures in Table 1 show the rates of dispersion in water and the "B" groups of figures show the micelle formation ability in bile acid salts solution.

The minute-particle dispersibility of the composition of Example 9 in water was measured by the method which is mentioned in the next paragraph.

The dissolution apparatus (manufactured by Toyama Industry, Japan) for the paddle method was charged with 900 ml of water. In this apparatus the composition of Example 9 which contained 500 mg of ubidecarenone was subjected to dissolution (100 rpm, 15 minutes). The resulting suspension was filtered successively through a series of 10 $\mu$, 3 $\mu$ and 0.45 $\mu$ millipore filters (manufactured by Nippon Millipore Company, Japan) and the transfer rate of ubidecarenone was measured by analyzing each suspension which passed through the filters. As the controls, the samples were tested which are mentioned in Example 5 of Japanese Laid Open Pat. No. 136911/77. The control samples were prepared as follows. Three g of ubidecarenone and some amount of hydroxypropylcellulose (HPC) were dissolved in 30 ml of ethanol. The resulting solution was adsorbed on 95 g of lactose. The powder thus prepared was molded by passing the mixture through a 20 mesh sieve and then drying the sample for 3 hours at 50° C. The amount of HPC was adjusted so that the content of HPC in the dry granules was either 3% or 7%. The results thus obtained are given in Table 2. The contents of HPC in Control 1 and Control 2 were 3% and 7%, respectively.

TABLE 2

| | Pore Size ($\mu$) | Transferring Rate (%) |
|---|---|---|
| Example 9 | 10 | 99.7 |
| | 3 | 99.1 |
| | 0.45 | 95.8 |
| Control 1 | 10 | 71.4 |
| | 3 | 31.4 |
| | 0.45 | 5.2 |
| Control 2 | 10 | 62.0 |
| | 3 | 15.7 |
| | 0.45 | 3.8 |

Note: The minute particle-dispersibility is indicated by the transfer rate data.

EXAMPLE 10

A liquid composition was prepared by dissolving with heat 10 g of ubidecarenone powder in the mixture of 10 g of octaglycerol monooleate (Santone® 8-1-0) and 20 g of decaglycerol decaoleate (Santone® 10-10-0).

EXAMPLE 11

Eight hundred grams of water, 30 g of lactose and 30 g of dextrin were added to 40 g of the liquid composition of Example 10. The resulting mixture was emulsified for 5 minutes at 12,000 rpm by a Polytron ® emulsifier (Polytoron Type 45/50 Kinematica GmbH, Swiss). A powdered composition was obtained after vaporizing water of the resulting emulsion by spraying.

For the purpose of clarifying the degree of bioavailability of the composition of Example 11, the ubidecarenone content in the blood of subject rats was measured 2 hours after each once-a-day oral administration of the pharmaceutical composition of Example 11 over five successive days. The results thus obtained are presented in Table 3. For Control 1 and Control 2 of this test, the same compositions which were used as Control 1 and Control 2 in the above-mentioned test of Example 9 were examined, respectively.

TABLE 3

| Composition Used | Ubidecrenone Concentration in Blood (ng/ml) |
|---|---|
| Example 11 | 6.19 ± 0.32 |
| Control 1 | 1.06 ± 0.18 |
| Control 2 | 1.01 ± 0.02 |

Additionally, in order to determine the degree of bioavailability of the composition of Example 11, as the lymphatics-absorbable drug composition, the transfer rate of ubidecarenone was measured.

The method of measurement used is as follows. The composition of Example 11 was administered orally to 5 Wister rats 24 hours after feeding of only physiological saline solution. Thereafter, the lymph of the 5 wister rats (250~300 g) was collected continuously separately through canulas, which had been connected to the lymphatics of rats, for 24 hours. Ubidecarenone in each collected lymph sample was measured by high speed liquid chromatography.

Control 1 of this test was the same as that of the previous test of Example 9. And Control 2 of this test was prepared as follows in accordance with the method of Example 1 of Japanese Laid Open Pat. No. 18914/81. Four grams of ubidecarenone and 28 g of monoolein were melted together and mixed in a mortar which was placed on a hot bath (ca. 60° C.). A powder having ubidecarenone adsorbed thereon was obtained by mixing the resulting melted mixture with 68 g of crystalline cellulose. The results thus obtained are shown in Table 4.

TABLE 4

| | Lymphatics Absorption Rate (%) |
|---|---|
| Example 11 | 9.51 (7.96~11.67) |
| Control 1 | 3.11 (1.98~4.31) |
| Control 2 | 5.45 (4.08~6.23) |

EXAMPLE 12

Fifty grams of griseofulvin, 15 g of polyethyleneglycol 400 (PEG-400), 20 g of decaglycerol decaoleate (Santone ® 10-10-0) and 30 g of decaglycerol monooleate (Santone ® 10-1-0) were dissolved in a mixed solution of ethanol and chloroform (1:1 by volume). The resluting solution was added to 200 g of purified water, in which 20 g of lactose and 10 g of porous silicic acid anhydride had been previously dispersed. The resulting system was emulsified with a Polytron ® emulsifier (described above) for 5 minutes at 12,000 rpm. A powdered composition was prepared after removing the water of the resulting emulsion by spraying.

Figure 4:
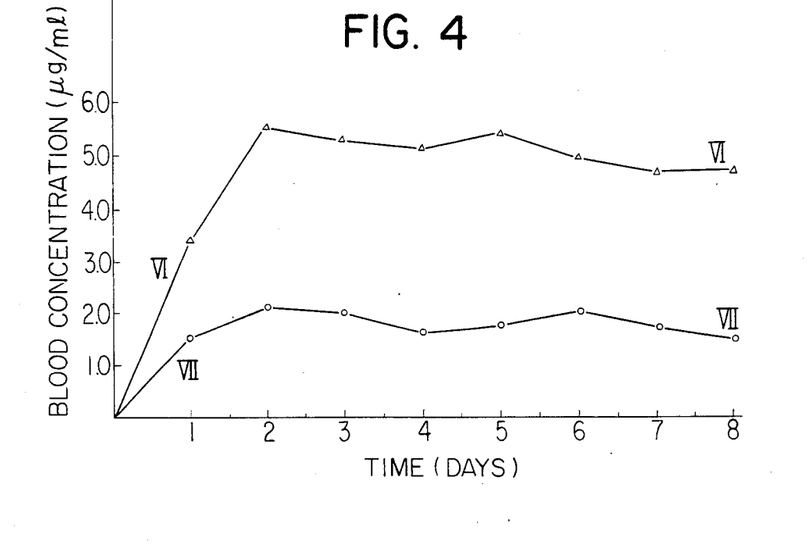
FIG. 4 is a diagram illustrating the results obtained from the test of Example 12.

The griseofulvin composition of Example 12 and as a control, powdered crystalline griseofulvin were separately administered orally to 3 adult male human subjects at a dose of 250 mg of griseofulvin four times a day. The griseofulvin content in the blood was measured daily. The results obtained are illustrated in FIG. 4 where the curves VI—VI and VII—VII represent the composition of Example 12 and the control crystalline powder of griseofulvin, respectively.

EXAMPLE 13

Fifty grams of kitasamycin was added to 30 g of pentaglycerol monooleate (SY-Glyster-MO-500, manufactured by Sakamoto Industry Co., Japan) and the mixture was dispersed with heat. Thereafter, the mixture was dissolved in a 200 g ethanol solution which contained 5 g of hydroxypropyl cellulose (Type L, manufactured by Nippon Soda Co., Japan). A powdered composition was obtained upon the vaporization of ethanol from this solution by spraying.

Figure 5:
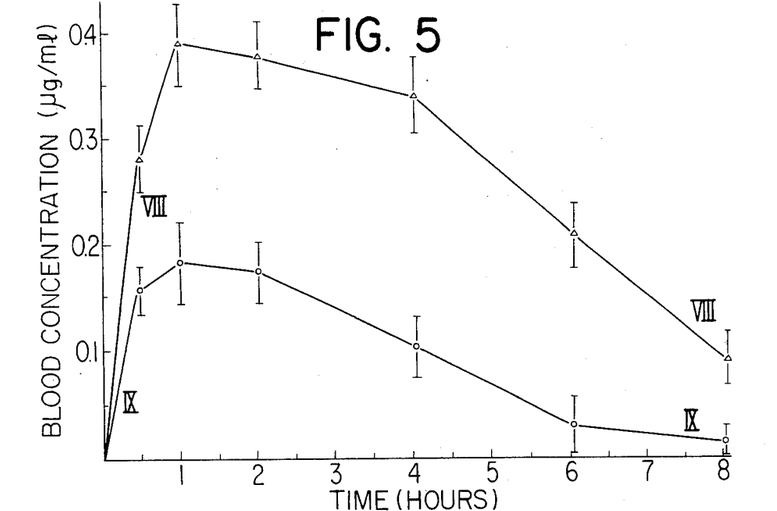
FIG. 5 is a diagram illustrating the results obtained from the test of Example 13.

The kitasamycin composition of Example 13 and a control cystalline powder of kitasamycin were separately administered orally to 6 adult male human subjects at a dose of 600 mg of kitasamycin. The kitasamycin content as it changed with lapses in time in the blood samples was measured. The results obtained are illustrated in FIG. 5 where the curves VIII—VIII and IX—IX represent the composition of Example 13 and the crystalline kitasamycin powder, respectively.

EXAMPLE 14

Eighty grams of phenacetin and 20 g of decaglycerol decaoleate (Santone ® 10-10-0) were dissolved in 500 g of chloroform. This solution was added to 100 g of a 5% hydroxypropyl cellulose (L Type, manufactured by Nippon Soda Co., Japan) aqueous solution which had been previously prepared. The resulting mixture was emulsified for 15 minutes by a ultrasonic homogenizer (Ultra Sonic Co., U.S.A.). A powdered composition was obtained after water and chloroform had been removed from the resulting emulsion by spraying.

Figure 6:
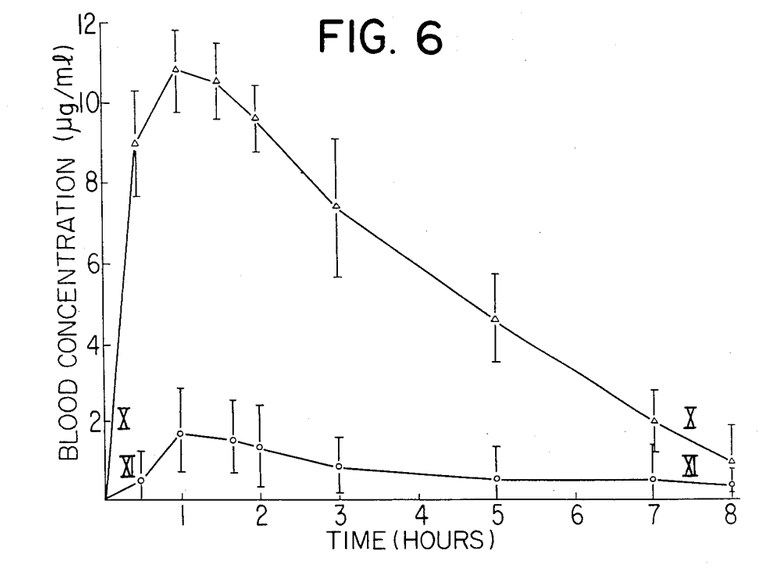
FIG. 6 is a diagram illustrating the results obtained from the test of Example 14.

The powdered composition of Example 14 and as a control, a commercial phenacetin crystalline powder, were separately administered orally to 6 adult male human subjects in a dose of 1.5 g of phenacetin. The phenacetin contents of blood samples were measured over lapsed periods of time. The results thus obtained are illustrated in FIG. 6 where the curves X—X and XI—XI represent the powdered compositions of Example 14 and the commercial phenacetin crystalline powder, respectively.

EXAMPLE 15

Twenty-five grams of cyclandelate were dissolved in a mixture of 25 g of decaglycerol decalinolenate (Decaglyn 10-Linolenate manufactured by Nikko Chemicals, Japan), 12 g of decaglycerol pentaoleate (Decaglyn 5-0), 23 g of triglycerol monooleate (SY-Glyster-MO-310 Sakamoto Pharm. Ind. Co., Japan) and 15.0 g of decaglycerol monolinolenate (Decaglyn 1-Linolenate) with heat. The resulting solution was encapsulated in soft capsules having a diameter of about 8 mm by the same process which is mentioned in Example 2. About 50 mg of cyclandelate was encapsulated in each capsule.

Figure 7:
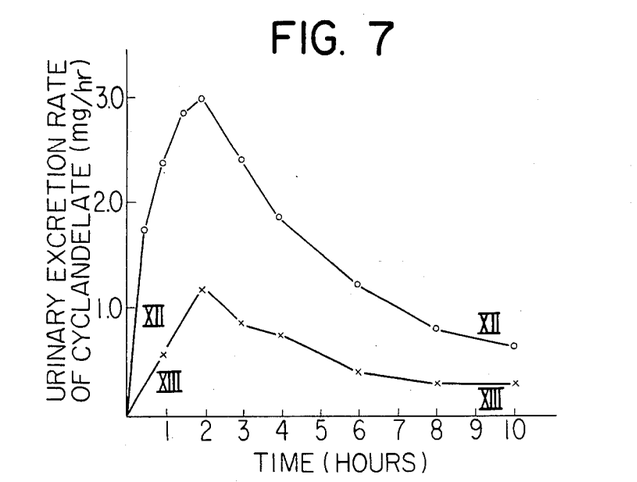
FIG. 7 is a diagram illustrating the results obtained from the test of Example 15.

To investigate the degree of bioavailability of the cyclandelate composition of Example 15, the capsules of Example 15 and, as a control, crystalline powder of cyclandelate were separately administered orally to 5 adult male human subjects at meal time at a dose of 100 mg as cyclandelate. Thereafter, the output of cyclandelate in the urine of the 5 adult male human subjects was measured with the passage of time. The results obtained are illustrated in FIG. 7 where the curves XII—XII and XIII—XIII represent the composition of Example 15 and the control crystalline powder of cyclandelate, respectively.

EXAMPLE 16

Forty-two grams of cinnarizine were dissolved in a mixture of 328 g of decaglycerol decalinoleate (Decaglyn 10-Linoleate, Nikko Chemicals, Japan), 150 g of decaglycerol pentaoleate (Decaglyn 5-0), 200 g of triglycerol monooleate (SY-Glyster-MO-310, Sakamoto Pharm. Ind. Co., Japan), 130 g of decaglycerol monolinolate (Decaglyn 1-Linolate) and 150 of 1-carvone with heat. The resulting solution was encapsulated in seamless microcapsules having a diameter of 2 mm by a Globex Mark II capsule-making apparatus which is shown in FIG. 1. The content of cinnarizine in each of these capsules was 3.5 w/w %.

Figure 8:
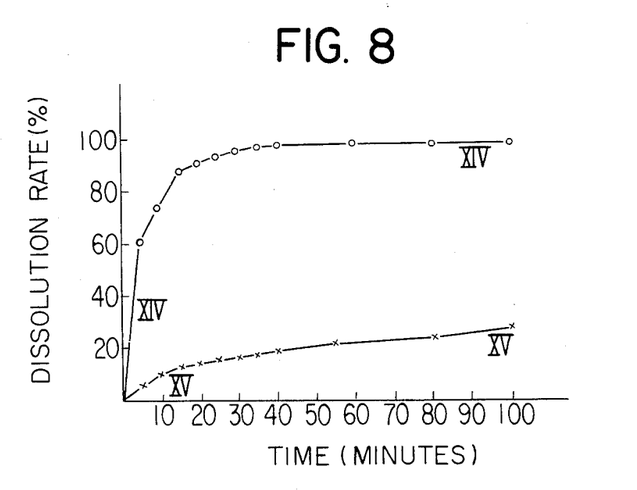
FIG. 8 is a diagram illustrating the results obtained from the test of Example 16.

The composition of Example 16 and as a control, a crystalline powder of cinnarizine, were subjected separately to dissolution test, which were conducted by the paddle method using a Freund/Jasco DT-300 Automatic Dissolution Tester (manufactured by Japan Spectroscopic Co., Ltd.). The dissolution test was conducted, using a sample which contained 25 mg of cinnarizine at 100 rpm of the paddle in 500 ml of dissolution-water. Cinnarizine in the dissolution-water was measured with the passage of time by 250 nm-ultraviolet light. The results thus obtained are illustrated in FIG. 8, where the curves XIV—XIV and XV—XV represent the composition of Example 16 and the control crystalline powder of cinnarizine, respectively.

EXAMPLE 17

Three hundred grams of d-α-tocopherol were dissolved in a mixture of 400 g of decaglycerol decalinolenate (Decaglin 10-Linolenate) and 1100 g of decaglycerol monolinolenate (Decaglin 1-Linolenate). Thereafter, the resulting solution was encapsulated in soft gelatin capsules by the same encapsulating process which is mentioned in the paragraph of Example 2. d-α-Tocopherol was present as 50 mg in each of the soft capsules.

The composition of Example 17 and as a control, commercial soft gelatin d-α-tocopherol-capsule, were subjected to dissolution tests which were conducted by the paddle method using the same dissolution tester as used in the test of Example 16. The dissolution test was conducted using a sample which contained 100 mg of d-α-tocopherol at a paddle rate of 150 rpm in 500 ml of dissolution-water, and d-α-tocopherol in the dissolution-water was measured with the passage of time by HPLC (high pressure liquid chromatography) using ethanol as a conveying liquid and using 254 nm ultraviolet light.

Figure 9:
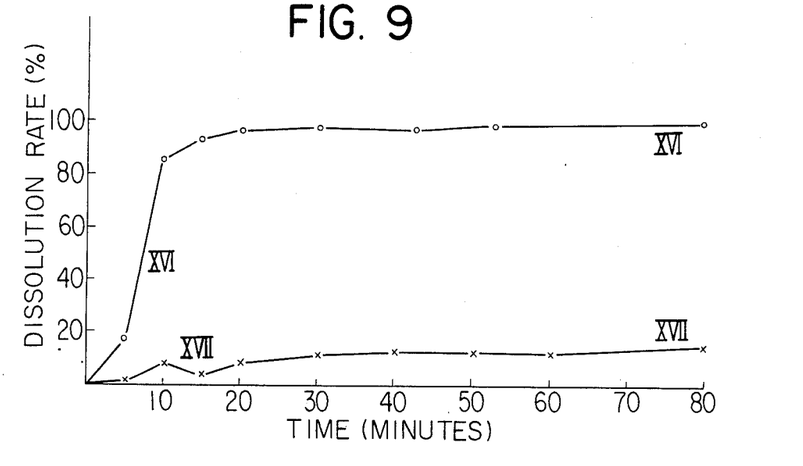
FIG. 9 is a diagram illustrating the results obtained from the test of Example 17.

The results obtained are illustrated in FIG. 9, where the curves XVI—XVI and XVII—XVII represent the composition of Example 17 and the control commercial soft gelatin d-α-tocopherol-capsule, respectively.

EXAMPLE 18

Figure 10:
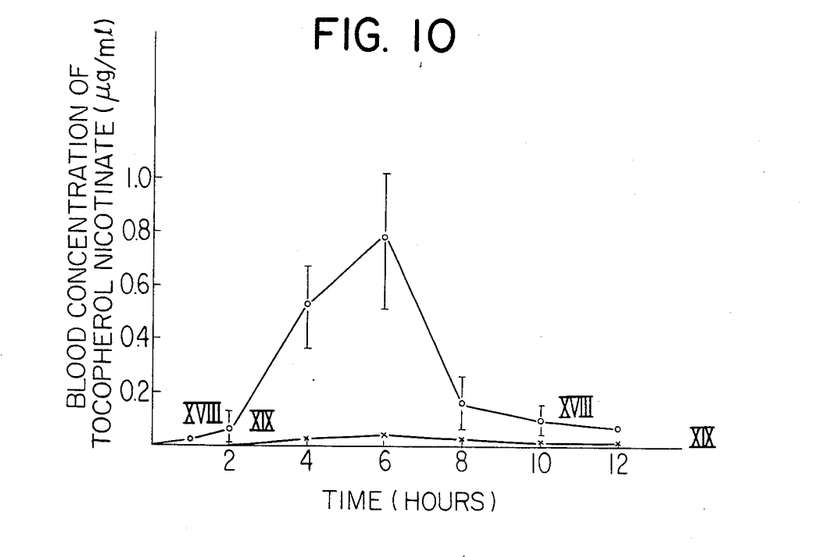
FIG. 10 is a diagram illustrating the results obtained from the test of Example 18.

Two hundred grams of α-tocopherol nicotinate dissolved in 200 g of decaglycerol-ricinoleate with heat. The resulting solution was encapsulated as soft capsules having a diameter of 9 mm by the same encapsulating process which is mentioned in the paragraph of Example 2. Two hundred mg of α-tocopherol nicotinate was present in each capsule. The composition of Example 18 and, as a control, a crystalline powder of α-tocopherol nicotinate were separately administered orally to 3 adult male human subjects at meal time at a dose of 600 mg as α-tocopherol nicotinate. Thereafter, α-tocopherol nicotinate in blood samples from the 3 adult male human subjects was measured with the passage of time. The results obtained are illustrated in FIG. 10, wherein the curves XVIII—XVIII and XIX—XIX represent the composition of Example 18 and the control crystalline powder of α-tocopherol nicotinate, respectively.

Having now fully described the invention, it will be apparent to one of ordinary skill in the art that many changes and modifications can be made thereto without departing from the spirit or scope of the invention as set forth herein.

What is claimed as new and desired to be secured by Letters Patent of the United States is:

1. A pharmaceutical composition which provides a high degree of bioavailability of cyclandelate when administered orally, which consists of a mixture of:
   (a) from 0.05 to 30 parts by weight of a polyglycerol ester of an unsaturated fatty acid or mixtures thereof per
   (b) 1 part by weight of cyclandelate.

2. The composition of claim 1, wherein the polyglycerol ester of an unsaturated fatty acid is a member selected from the group of esters which have 8 to 22 carbon atoms in the unsaturated fatty acid portion and 2 to 20 glycerine units.

3. The composition of claim 2, wherein the unsaturated fatty acid of the polyglycerol ester is oleic acide, ricinoleic acid, linolenic acid or linoleic acid.

4. The composition of claim 1, wherein said cyclandelate is dispersed in a polyglycerol ester of an unsaturated fatty acid.

5. A pharmaceutical composition which provides a high degree of bioavailability when administered oraly which consists of 1 part by weight of cyclandelate adsorbed on a powder wherein said cyclandelate adsorbed on the powder is dispersed in 0.05 to 30 parts by weight of a polyglycerol ester of an unsaturated fatty acid.

6. The composition of claim 5, wherein the powder is lactose-powder β-cyclodextrin, microcrystalline cellulose, starch, wheat flour, dextrin, cellulose-powder, powdered silicon dioxide or mixtures thereof.

* * * * *